United States Patent [19]

Watrous

[11] Patent Number: 5,564,302

[45] Date of Patent: Oct. 15, 1996

[54] ORTHOPEDIC BONE PLATE BENDING IRONS

[76] Inventor: Willis G. Watrous, 2545 Birch La, Eugene, Oreg. 97403

[21] Appl. No.: 500,773

[22] Filed: Jul. 11, 1995

[51] Int. Cl.⁶ .................................................. B21D 7/00
[52] U.S. Cl. ................................. 72/458; 72/479
[58] Field of Search ................. 72/458, 459, 479; 140/106

[56] References Cited

U.S. PATENT DOCUMENTS

| | | | |
|---|---|---|---|
| 124,362 | 3/1872 | Kernon | 81/15 |
| 238,582 | 4/1881 | Grubb | |
| 1,286,488 | 12/1918 | Amberg | |
| 1,531,001 | 3/1925 | Graves | |
| 2,087,125 | 7/1937 | Smith | 140/106 |
| 2,737,835 | 3/1956 | Herz | 81/15 |
| 2,772,587 | 12/1956 | Woodring | 81/15 |
| 2,800,818 | 7/1957 | Larson | 81/15 |
| 3,610,019 | 10/1971 | Denninger | 72/386 |
| 3,824,834 | 7/1974 | Durham | 72/387 |
| 3,866,458 | 2/1975 | Wagner | 72/459 |
| 3,901,064 | 8/1975 | Jacobson | 72/388 |
| 4,474,046 | 10/1984 | Cooke | 72/409 |
| 4,858,665 | 8/1989 | Miller et al. | 72/458 |
| 5,113,685 | 5/1992 | Asher | 72/458 |
| 5,161,404 | 12/1992 | Hayes | 72/458 |
| 5,389,099 | 2/1995 | Hartmeister | 606/61 |

FOREIGN PATENT DOCUMENTS

| | | | |
|---|---|---|---|
| 0479753 | 7/1929 | Germany | 72/458 |
| 4300316 | 7/1994 | Germany | 72/458 |

OTHER PUBLICATIONS

Anthology of Orthopedics, Mercer Rang, 1966, p. 187.

*Primary Examiner*—David Jones
*Attorney, Agent, or Firm*—Marger, Johnson, McCollom & Stolowitz, P.C.

[57] ABSTRACT

The present invention is a simple machine that permits the concentrated application of a bending moment to a stiff metallic bone plate. The present invention permits bends along three orthogonal torsional axes. The present invention can be scaled so that modest sized operators can bend the most stout bone plates. The bending moments are transmitted to the bone plates through the edges of curved apertures so that the built in transverse curvature of the plate is not crushed with resulting weakening of the plate. Finally, the apertures are rotated and angled to provide comfortable hand clearance and to permit efficient application of muscle force by the operator.

26 Claims, 13 Drawing Sheets

RECONSTRUCTION PLATE

Fig. 6
PRIOR ART
SLOTTED MANUAL
BENDING TOOL
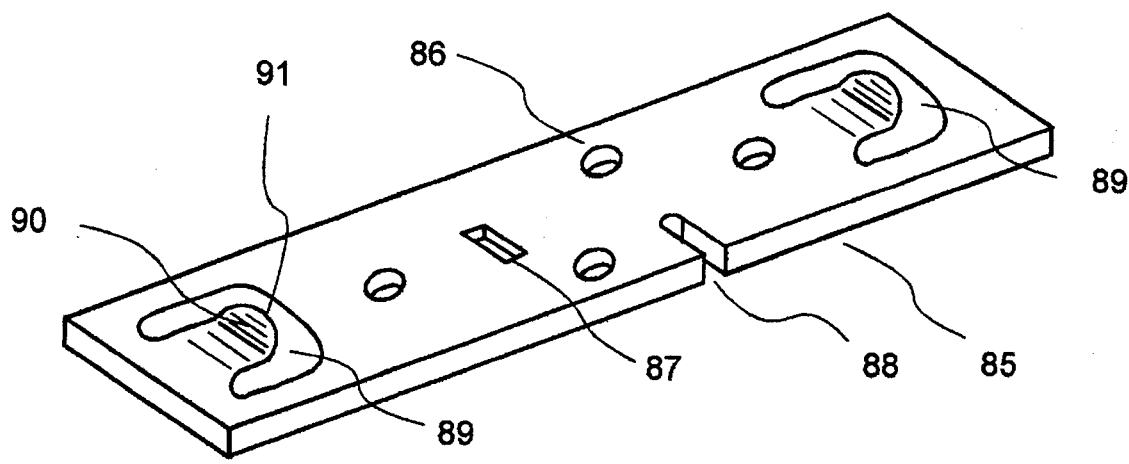
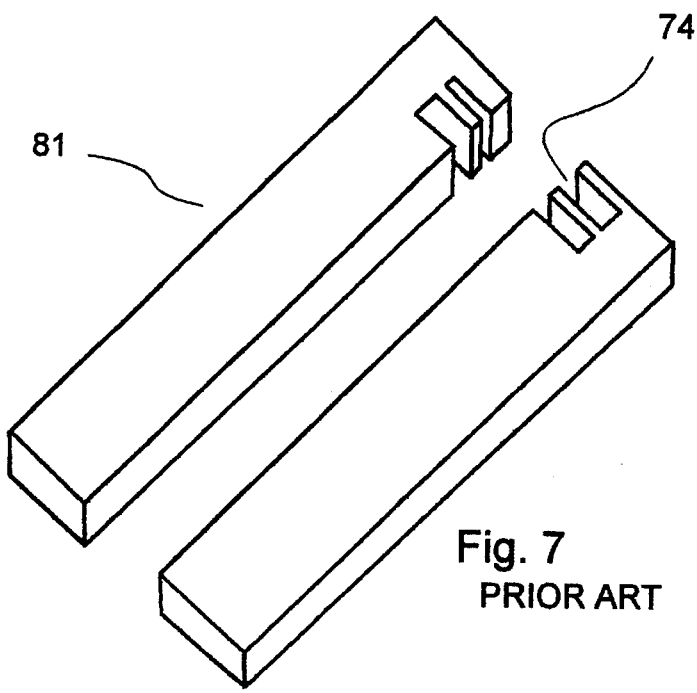
Fig. 7
PRIOR ART Fig. 8 PRIOR ART PLATE BENDING PRESS

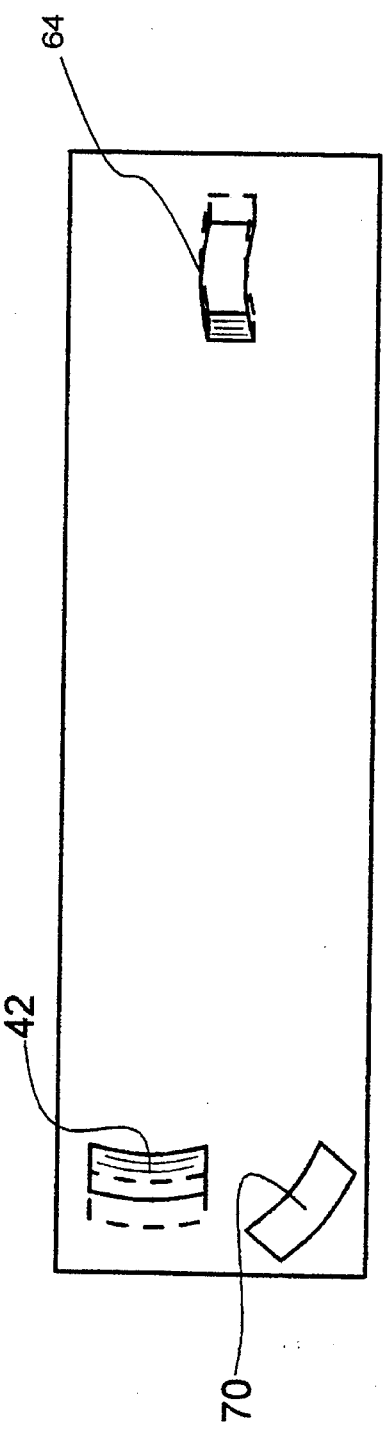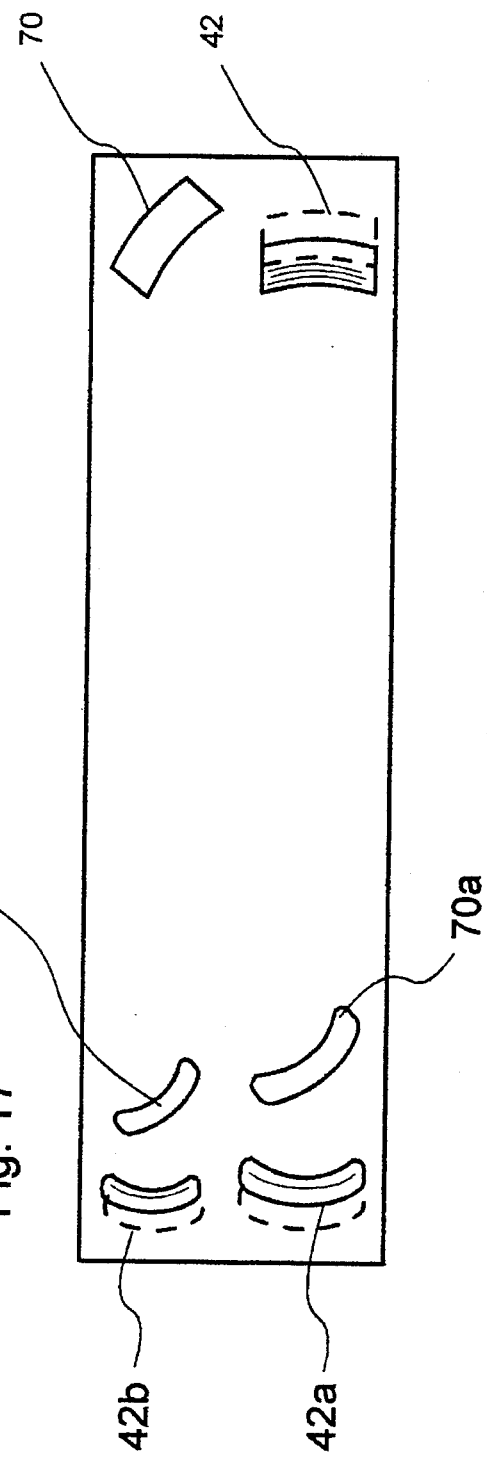

ORTHOPEDIC BONE PLATE BENDING IRONS

FIELD OF THE INVENTION

The present invention relates to hand tools that are routinely used to bend and twist metallic plates in the performance of orthopedic surgery.

BACKGROUND OF THE INVENTION

In 1905, Sir William Arbuthnot Lane introduced the use of flat linear steel plates 20 with round screw holes 21 and hole bosses 22, shown in FIG. 1, to surgically repair broken bones. This introduction was motivated by the poor results following cast treatment of many of these fractures. The bone plates must be deformed to conform to the preinjury shape of the bone. Dr. Lane bent and twisted the bone plates with the simple tool shown in FIG. 2. Two of these tools used together permit bending of a bone plate out of the plane of the plate and twisting along the axis of the plate. They are not adequate for bending bone plates in the plane of the plate. Contemporary surgeons use an identical tool to twist the modern bone plates shown in FIGS. 3 and 4, and to bend those plates, but only out of the plane of the plate. Similar tools have long been used by smithies (U.S. Pat. No. 124,362 to Kernon in 1872).

Bend in the plane of the plate is occasionally necessary. For those cases the deliberately weakened plate seen in FIG. 5, known as a reconstruction plate, is used. This plate is often bent with gloved hands or a soft tissue clamp. From time to time such plates bend or break after implantation, causing a loss of fracture fixation. A bender able to bend a strong dynamic compression plate in the plane of the plate would be a great benefit for such cases.

The modern bone plate known as a dynamic compression plate and shown in FIG. 3 includes elongated holes 78 with sloped side walls to compress broken bone ends together. The plates have a transverse curve 9 to improve stiffness, strength and conformity to the bone. Similar bone plates are made in several sizes. Each size is made by several manufacturers. There are subtle differences between manufacturers plates particularly in length and the shape of their longitudinal edge. Modern plates, however, are weakest at the screw holes since the reinforcing bosses 22 around the screw holes 21 of the early bone plate of FIG. 1 have been eliminated in modern plates. Thus, a disproportionate amount of bend takes place at the screw holes regardless of where the bend is desired.

The prior art tool of FIG. 2 has distinct disadvantages when used to bend modern orthopedic bone compression plates. Since a pair of tools are typically used to bend many sizes of plates, the single slot 74 in the bending iron fits the plates poorly. The top jaw 75 is also quite thick to compensate for the weakness of the open slot design. When bending forces are applied, the thick upper jaw and widely abducted handles 76 result in bending forces being applied over an appreciable length of the plate. Additionally, the flat jaw faces crush the transverse curvature of the plates, particularly when used to bend the round holed plates shown in FIG. 4.

Modern plate bending irons 81, shown in FIG. 7, are improved only in that they are scaled for smaller plates. They further suffer from shallow slots so that the sterile plate being bent is prone to pop out and land on the floor if a second operator doesn't hold onto it. Further, the bending irons of FIG. 7 are supplied in pairs where the end slot of one iron is used with the second slot of the second iron, aggravating the tendency to apply force diffusely and bend the plate predominantly where it is weakened by the screw holes.

Prior art does exist addressing the problem of bending elongate metal rods and plates that, for various reasons, has not been of benefit for bending bone plates.

U.S. Pat. No. 2,737,835 to Herz in 1956 discloses a slotted plate bender that principally adds a protractor to measure the bend angle.

U.S. Pat. No. 5,389,099 to Hartmeister in 1995 discloses a slotted round rod bender with an angle near its working end. This is meant to bend a rod already anchored into a patient. The bend helps by increasing the room for the operator's hands on closely approximated tools. The slot axis is, however, perpendicular to the axis of the working end of the tool, requiring some tool end separation. As a result, bending moments are still imprecisely applied over an extended length of the rod. Broad application of bending moment is less of a problem for rods than for bone plates because rods are not weakened by screw holes. The rod bender is slotted and inherently weaker than a pierced bender and hence requires thicker metal at its distal end, further aggravating the imprecise application of bending moments.

U.S. Pat. No. 5,161,404 to Hayes in 1992 discloses a round rod bender with a long angled tip and a hole down the axis of the tip. The bender is well suited to making a single bend of up to 180 degrees in a round rod. However, once a small bend is made the rod will not advance through the bender and neither a diffuse bend nor a second bend can be made. The tool is expensive to made and difficult to clean.

U.S. Pat. No. 3,901,064 to Jacobson in 1975 from the general metalworking art discloses a bender with many parts that immobilizes a malleable strip by clamping it to a base and bending it around a radius pin in the plane of that strip using a long slotted pivoting lever to develop adequate bending moment. The device performs its limited function but it is complex, expensive, and difficult to clean of surgical blood and tissue.

U.S. Pat. No. 5,113,685 to Asher et al. in 1992 discloses a bender for rods and flat plates. A plate bending aperture near the end of the bender is closed at both ends, strengthening it and permitting the aperture to be closer to the end of the bender and somewhat improves the localization of bending moment. The apertures are, however, perpendicular to the plane of the bender and hence do not maximally localize bending moments. The apertures have straight sides with half round ends and hence will flatten the curvature and weaken plates with transverse curves. The apertures are not proportioned for and will not accommodate the very common and useful plates that are made from one third or one half of the circumference of a round tube 30, seen in FIG. 4. The two slots per bender are parallel to and perpendicular to the long axis of the bender. Hence, when stout flat plates are being twisted, the held surfaces of the benders will be adjacent to each other, separated by 90 degrees or separated by 180 degrees. None of these hand positions permits efficient application of arm muscle force to generate a twisting moment.

U.S. Pat. No. 3,866,458 to Wagner in 1975 describes a very complex bender for fixation plates for fractured hips. One half of that bender has long curved jaws that tighten on the curved face of the hip fixation plate. The second half of the bender has a hinged clamp and nipple that mates with a screw fixation hole in the plate. Handles at right angles to the jaws permit bending in one plane only. Half of the bender will only grasp the side plate at a screw hole, roughly every centimeter, not where a bend would best adapt the plate to the shape of the broken hip to be fixed. Once the plate is bent, the long jaws of the second half of the bender will not grasp the plate without deforming the earlier bend. The benders are complex, expensive and bulky. Their broad faces preclude close apposition and well localized bends if bends of more than a few degrees are going to be made.

U.S. Pat. No. 2,800,818 to Larson in 1957 discloses a kit for forming peg board hangers that includes pieces of wire of several diameters, thin straps with a concave-convex transverse cross section and a tool 85 of flat soft steel. The tool includes multiple round 86 and square holes 87 and edge slots 88 for holding round and square wires while they are being bent. More complex, generally C-shaped slots 89 are present at the two ends of tool 85. Each slot has a curved edge which conforms with the convex side of a strap. A central tab 90 having a curved end 91 which conforms with the concave side of the strap is bent upwardly out of the plane of the bar. This design supports the thin transversely curved strap as it is bent through modest angles. The design is inherently unable to cope with stout transversely curved plates and it does little to localize bending moment so that bends will occur where they are desired rather than where the strap is weakened at a screw hole.

An alternative tool known as a plate bending press is shown in FIG. 8 and has enough leverage to bend very stout plates between a curved ram 83 and a curved anvil 82. However, it is even more imprecise than plate bending irons in its application of force and in the curve it imparts to the plate. Furthermore, it requires maintenance and cannot twist the plate.

Accordingly, a need remains for an orthopedic bone plate bender which concentrates force over a short length of the plate, which will support rather than crush the transverse curve of the plate, and which supplies an increased amount of bending force so that a moderate sized operator can bend the most stout bone plates.

SUMMARY OF THE INVENTION

It is an object of the invention to apply bending moments over a short length of the bone plate in order to make precise bends.

Another object of the invention is to support rather than crush the transverse curve of the plate.

A further object of the invention is to allow a moderate sized operator to twist a stout bone plate and bend it in two planes.

The present invention provides a new and improved method and apparatus for use in plastically deforming orthopedic bone plates to a desired configuration for compression of fractured bones. The apparatus for plastically deforming the bone plates includes a pair of elongate rigid bending members, each having an enclosed aperture extending through the member adjacent one end. The aperture on each member is sized to receive therethrough a segment of a particular type of bone plate and is crescent-shaped to support the transverse curve found in conventional bone plates.

In one embodiment, the aperture extends downward through the member at an angle to allow the members engaged with a bone plate to extend away from one another. Moving the bending members through an arcuate curve applies bending forces perpendicular to a principal plane of the bone plate located between the segments received in the apertures. In an alternate embodiment of the invention, the aperture opening located on the surface of the bending tools are rotated at a positioning angle and extend straight through the member. Moving the bending member in an arcuate curve along their lateral axis applies twisting forces to the bone plate around its major axis. A third embodiment orients the symmetric axis of the aperture perpendicular to the long axis of the member for bending of an engaged bone plate in its principal plane. An additional embodiment includes several embodiments in the same tool.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 6 illustrates a prior art slotted manual bending tool for peg board hangers.

FIG. 7 illustrates a pair of prior art contemporary plate bending irons with slots for bending small plates.

FIG. 16 is a top view of an alternate embodiment of the present invention that can bend a dynamic compression plate in two planes and twist it along its axis.

FIG. 17 is a top view of a preferred embodiment of the present invention that can bend three different bone plates perpendicular to the plane of the plate and twist the same three bone plates along their long axes.

DETAILED DESCRIPTION

Figures 1, 2:
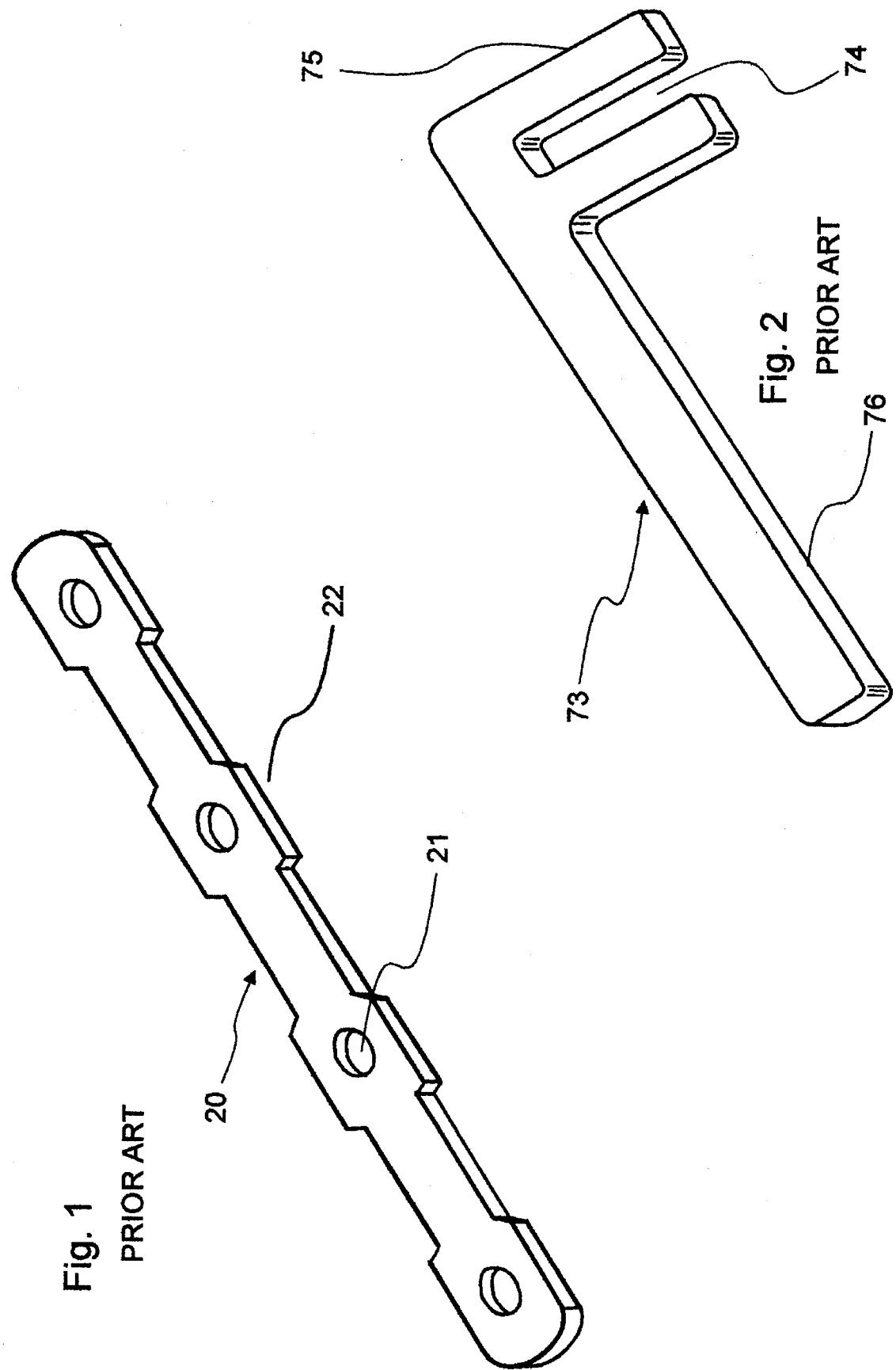
FIG. 1 illustrates a bone plate circa 1905 with four fixation screw holes in perspective view.
FIG. 2 illustrates a prior art plate bending tool in perspective view.
Figure 3:
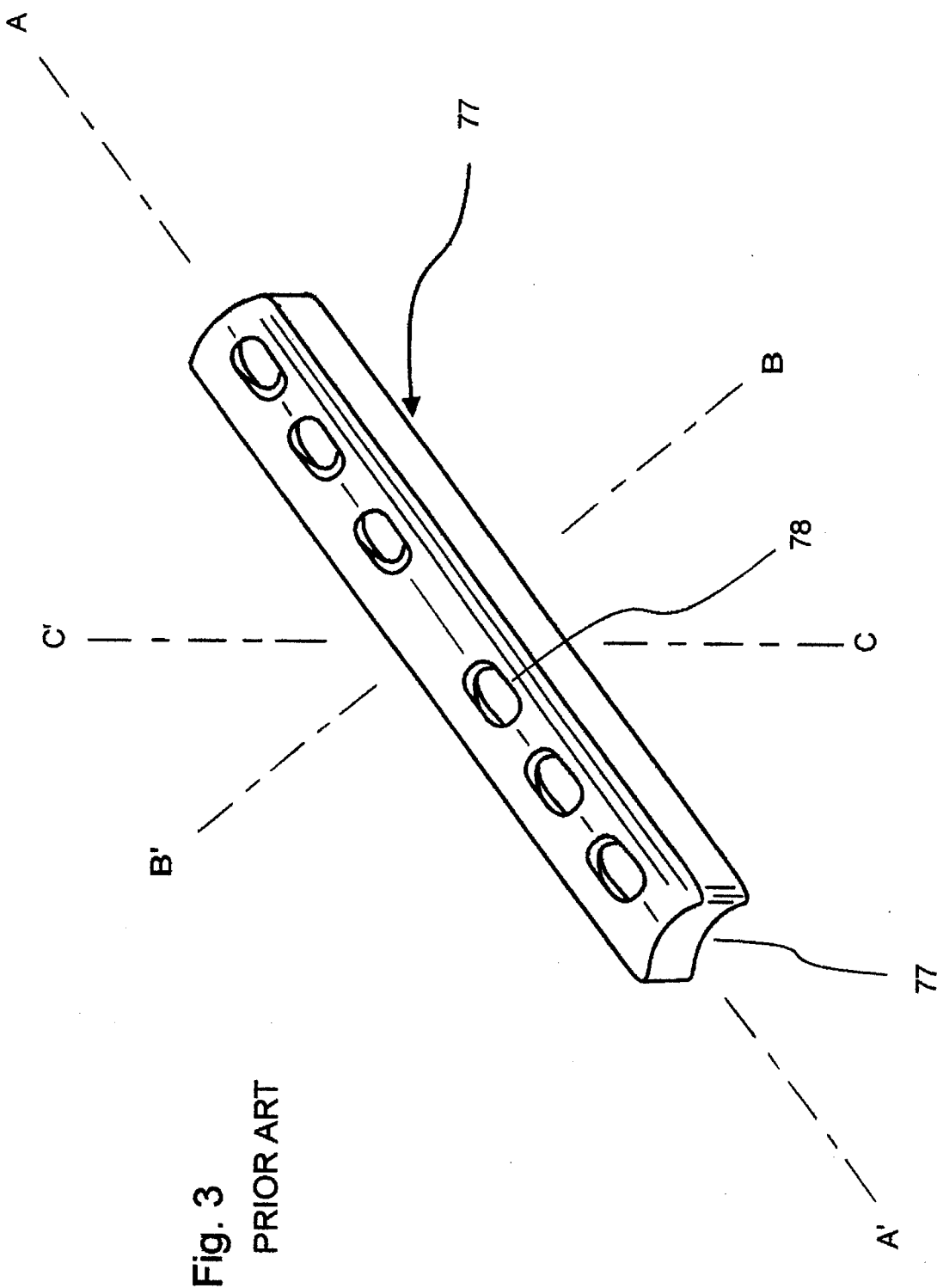
FIG. 3 illustrates a contemporary bone plate with transverse curvature and sloped side walls to compress broken bone ends together.
Figure 5:
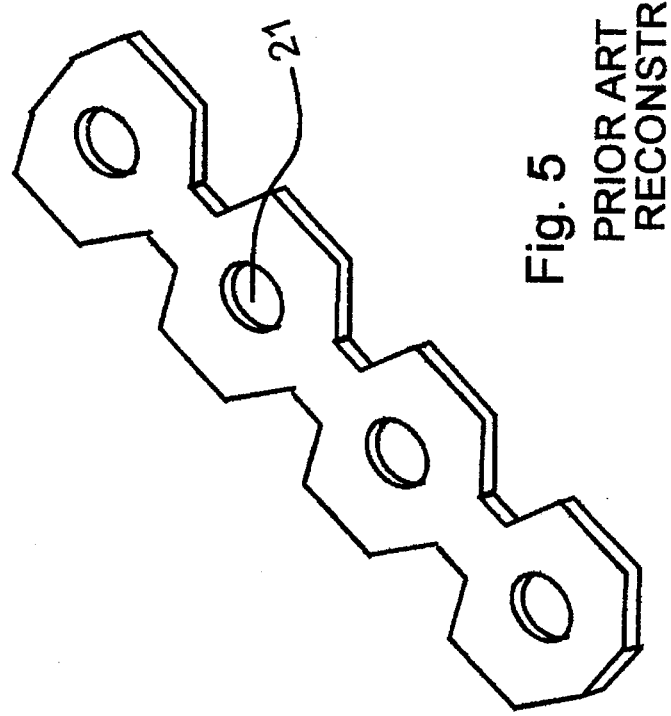
FIG. 5 illustrates a prior art reconstruction plate.
Figure 4:
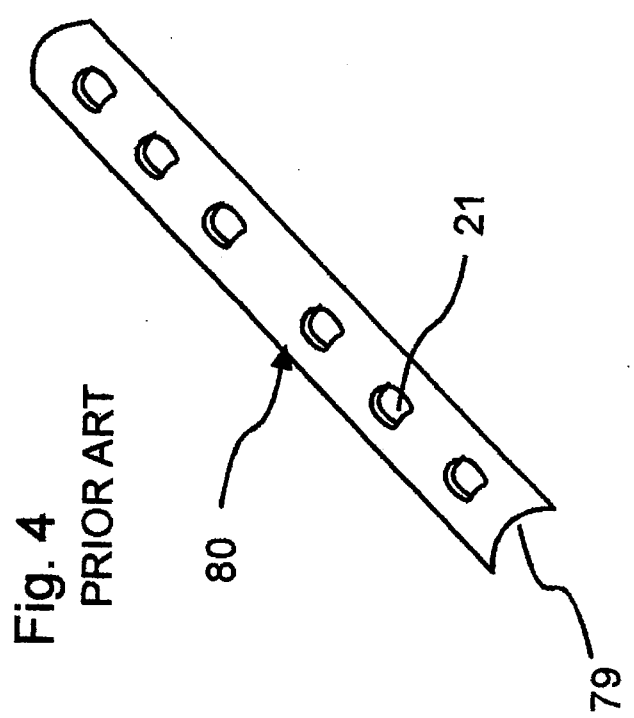
FIG. 4 illustrates a contemporary "round holed plate".
Figure 8:
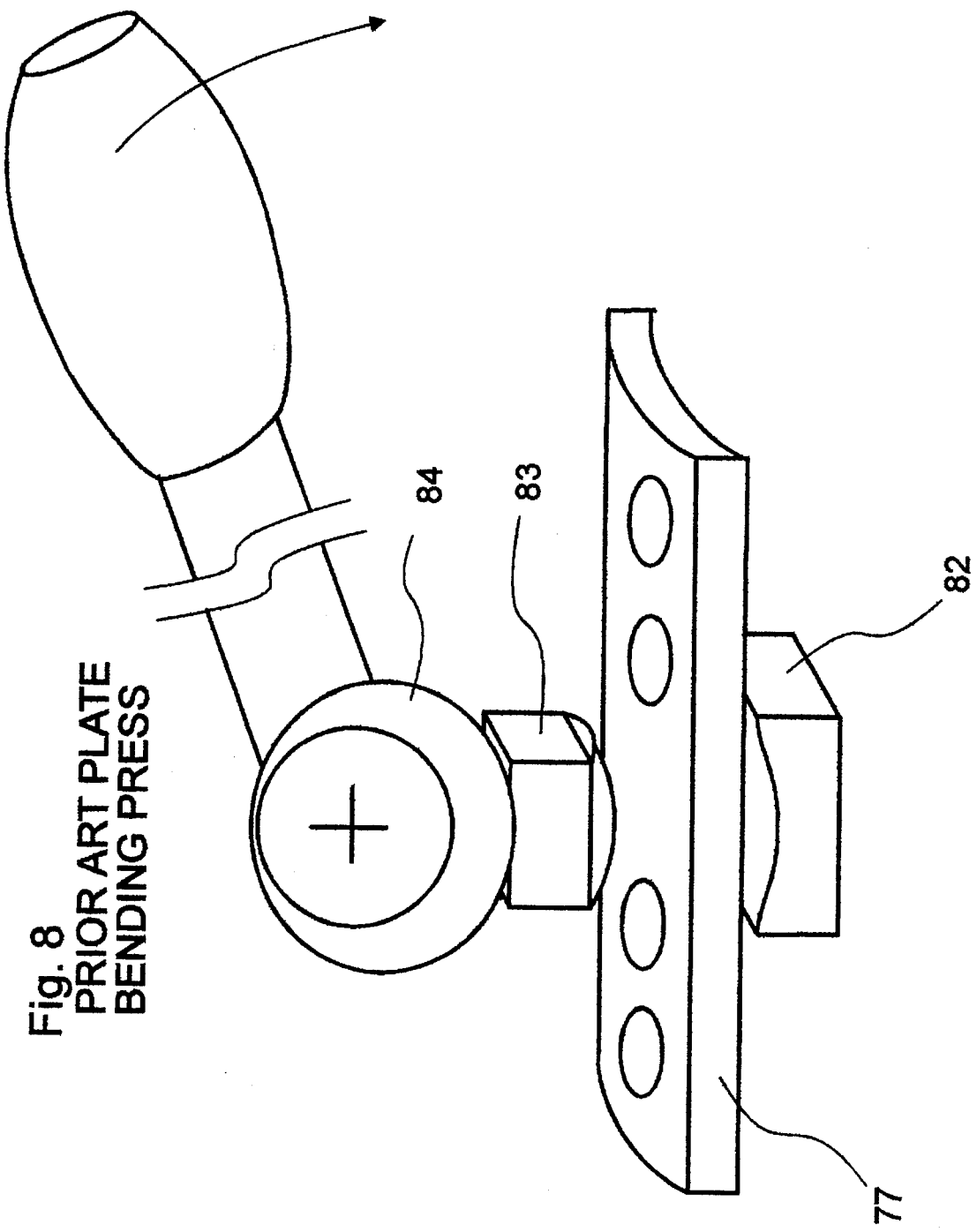
FIG. 8 is a schematic illustration of a prior art plate bending press.

FIGS. 3 and 4 show conventional bone plates commonly used in surgery to bind fractured bones. Such plates are typically bent along any of three different axes to conform to the curvature of a patient's bone. Referring to FIG. 3, line A'A is the longitudinal axis of the plate. Line B'B is the transverse axis of the plate. Lines A'A and B'B together define the principal plane of the plate. Line C'C is perpendicular to the principal plane of the plate. A bend made around line C'C or any parallel line is a bend in the principal plane of the plate. A bend made around line B'B or any parallel line is a bend out of the principal plane of the plate. A bend made around line A'A is twist along the major axis of the plate.

Figure 9:
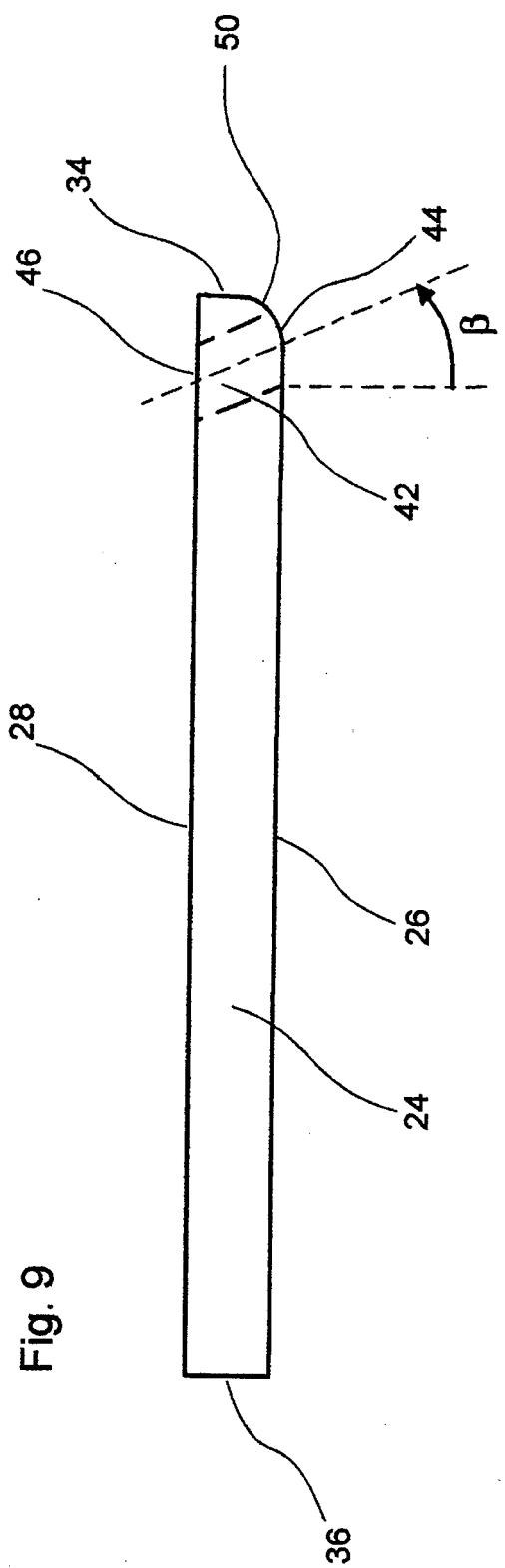
FIG. 9 is a side view of a plate bending tool in accordance with the present invention that is suitable for bending a dynamic compression plate perpendicular to its principal plane.
Figure 10:
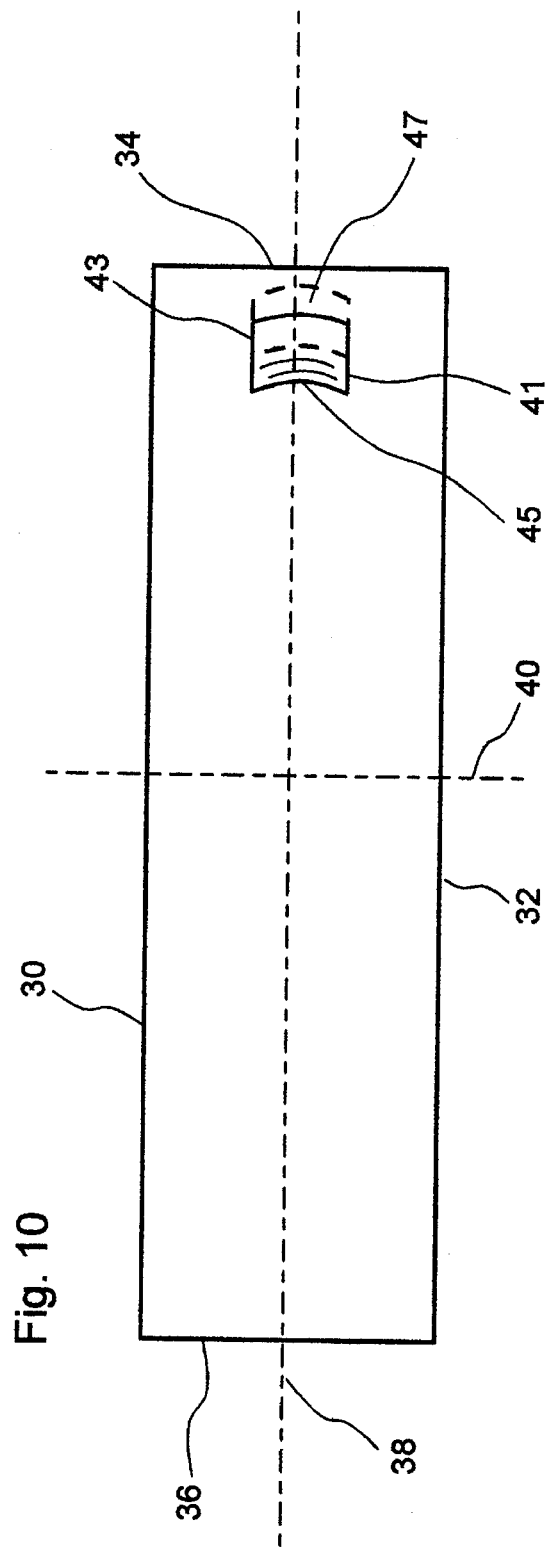
FIG. 10 is a top view of the plate bending tool of FIG. 9 in accordance with the present invention.

FIGS. 9 and 10 show the preferred embodiment of the orthopedic plate bending tool. The tool is comprised of an elongate member 24 having first and second major surfaces 26, 28, first and second longitudinal edges 30, 32 and first and second lateral edges 34, 36. Member 24 also has a longitudinal axis 38 passing from edge 34 to edge 36 and a lateral axis 40 passing from edge 30 to edge 32. A fully enclosed aperture 42 is located adjacent lateral edge 34 and passes from a first aperture opening 44 located on first major surface 26 to a second aperture opening 46 located on second major surface 28. When in use, lateral edge 34 forms a working end of the tool and lateral edge 36 forms an operating end.

Figure 18:
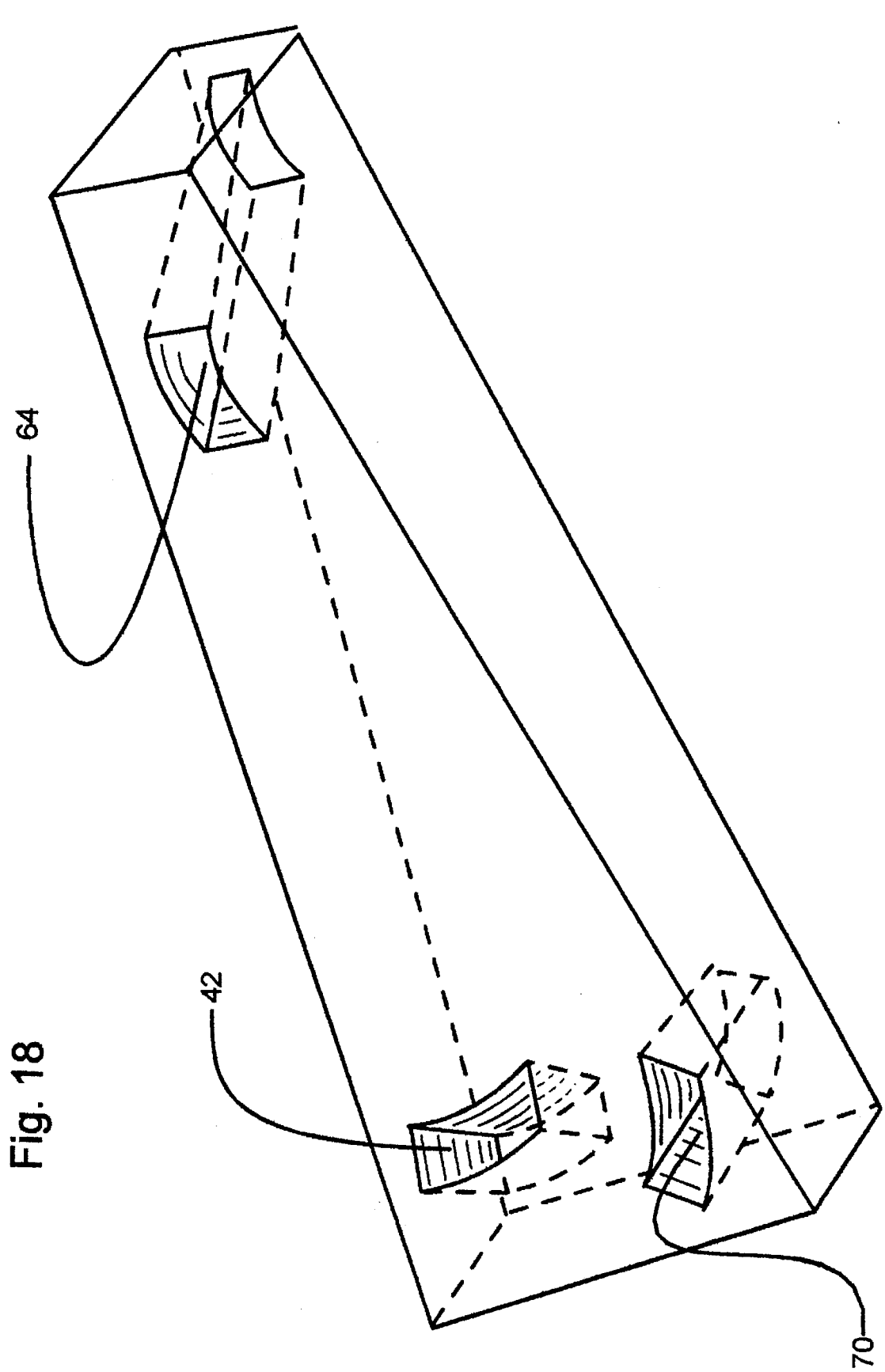
FIG. 18 is a view of an additional embodiment of the invention for bending and twisting a very stout dynamic compression plate.

Each bending member 24 should preferably be constructed of the same material as the plates which are to be bent by the tool. A 316L stainless steel would be used most often, since the majority of bone plates are made of 316L-type stainless steel. The member can also be made of alternate materials such as titanium, a titanium alloy, or a cobalt, chromium, molybdenum alloy in approximate ratios of 65%, 30%, and 5% respectively, or other alloys used to make orthopedic implants. Member 24 proportioned for smaller plates has a preferably rectangular cross-section, thus resulting in surfaces 26, 28, 30 and 32 being substantially planar. The cross sectional thickness of member 24 is determined by the thickness of the plate to be bent and its composition, but should generally be of a sufficient thickness to resist deformation or breaking when used to bend a dynamic compression plate. As shown in FIG. 18, elongate member 24 can be of increasing thickness and/or increasing width along its length for improved strength and durability.

In small volume production, the apertures are preferably made by wire electric discharge machining. In large volume production, the apertures are preferably made by ram electric discharge machining, or by electrochemical machining. Alternatively, the apertures could be milled and broached, or made by other methods well known in the metalworking art.

Figure 10A:
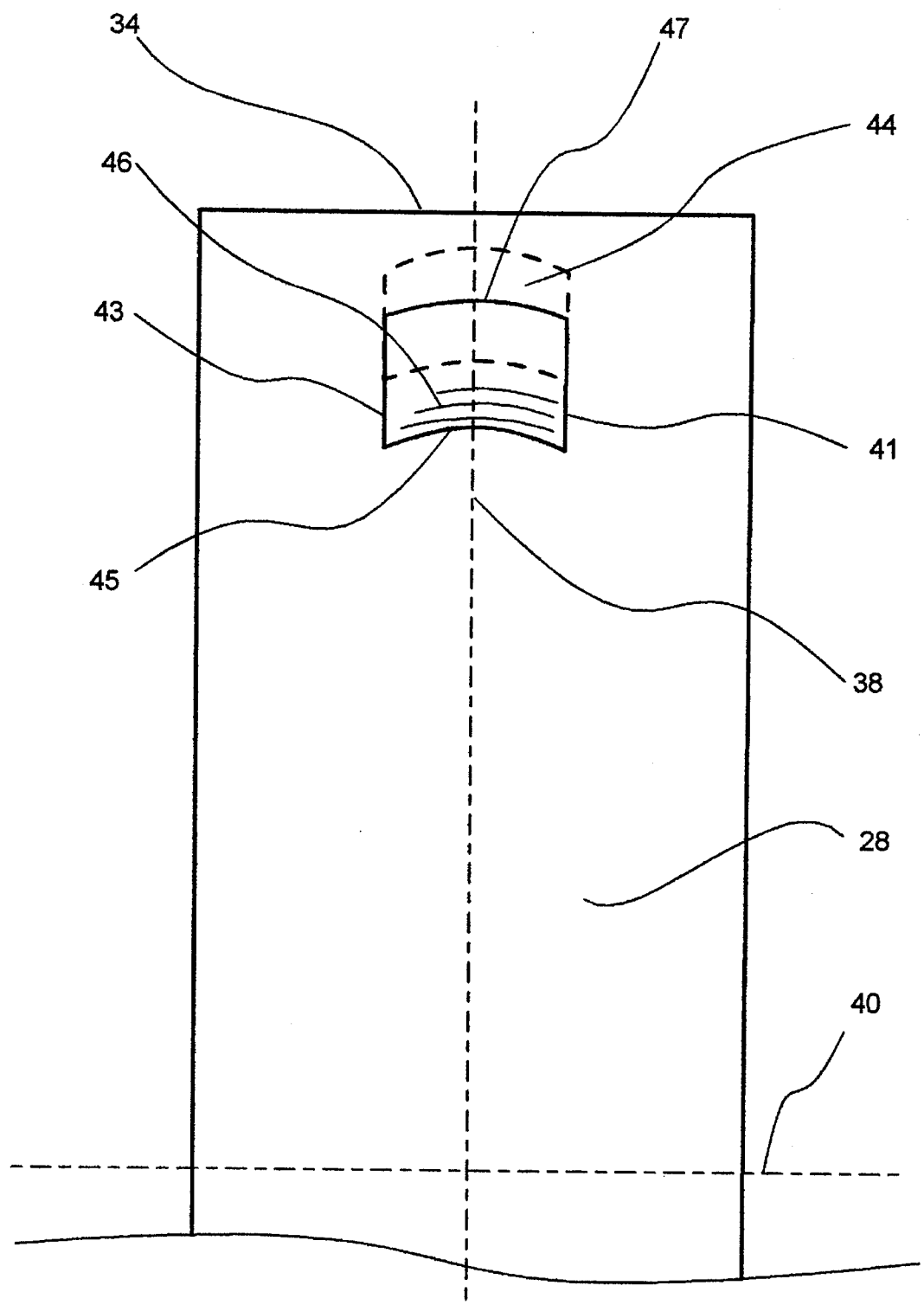
FIG. 10A shows a magnified view of the aperture opening of FIG. 10.

FIG. 10A shows a magnified view of aperture opening 46. Aperture opening 46 (like opening 44 located on the opposite face of the tool member) is shaped to be proportional to the cross section of the bone plate. Preferably, openings 44, 46 are approximately one to 100 mils larger than the compression plate cross section to allow easy passage of the compression plate through the aperture opening and into the aperture even after the plate has been bent into a useful shape. The cross section of aperture opening 46 shown in FIG. 10A is preferably crescent shaped, having two sides 41, 43 which are straight and parallel in this embodiment and will accommodate slight variation in plate edge shape from various plate vendors. Aperture opening 46 further has two substantially parallel curvilinear sides 45, 47, to receive the contemporary bone plate shown in FIG. 3 and is substantially symmetric about an aperture axis 48. When the plate is inserted through the aperture, curvilinear side 45 supports the transverse curve 79 of the plate to keep it from being flattened or crimped during the bending process at a weakened location around holes 78.

Figure 11:
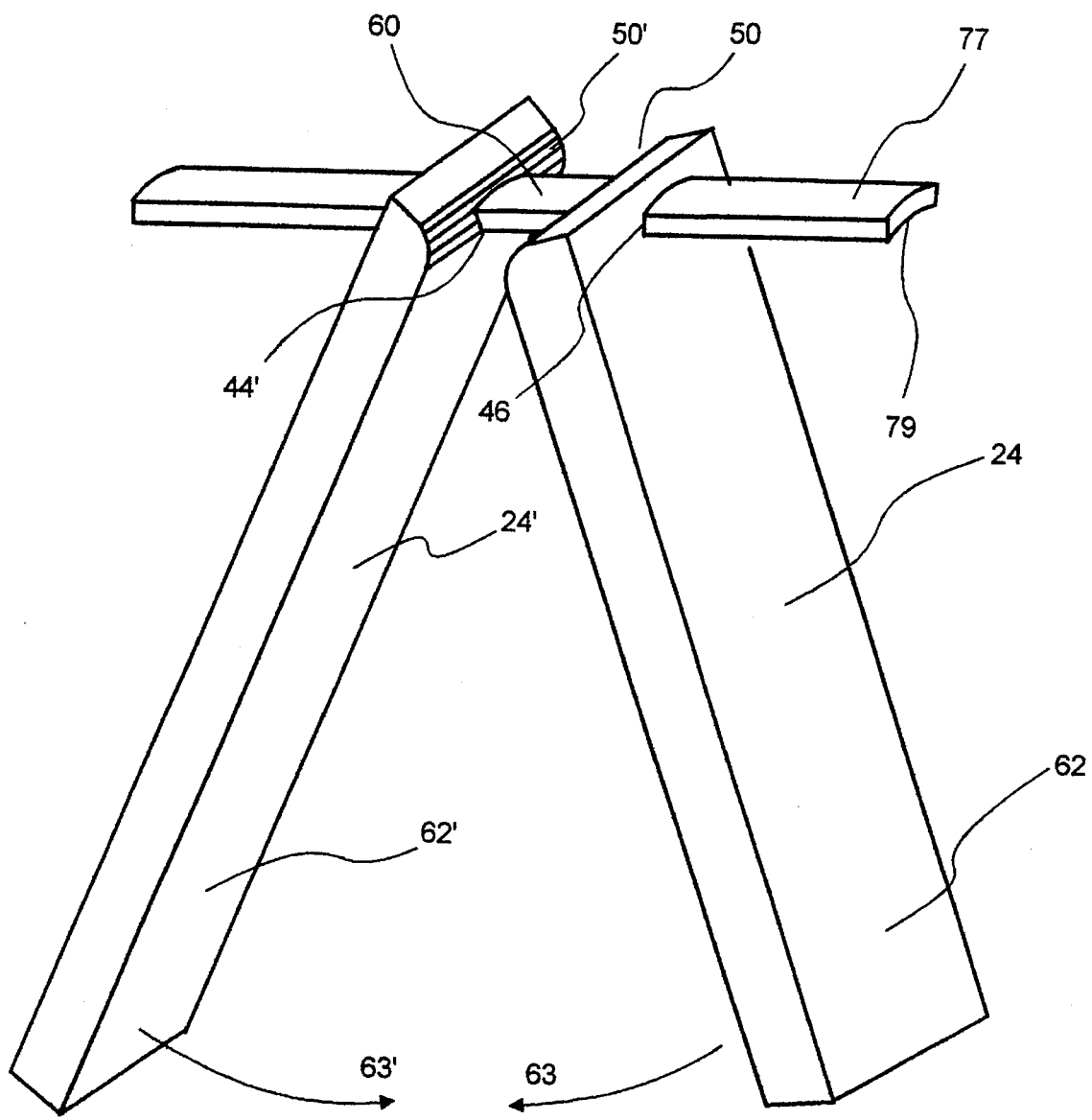
FIG. 11 illustrates the use of the bending tools of FIG. 9 positioned to bend a dynamic compression plate perpendicular to the plane of the plate.

Aperture 42 within the bending tool of FIGS. 9 through 11 is oriented laterally so that the axis B'B within the principal plane of the compression plate of FIG. 3 is orthogonal to the long axis of the bending tool. The aperture slopes obliquely downward at a predetermined angle β between 5 and 60 degrees and preferably between 10 and 45 degrees. The edge of working end 50 of the tool 24, formed by the intersection of major surface 26 with lateral edge 34, is radiused to permit closer apposition of the working ends 50, 50' of the tools when used as shown in FIG. 11. (Although for clarity close apposition is not shown)

FIG. 11 shows the preferred partial embodiment of the invention used to bend a compression plate perpendicular to the principal plane of the plate. Compression plate 77 is inserted through the downward sloping apertures 42, 42' (with openings 46, 44' seen) on each of the pair of bending tool members 24, 24'. In this position, the working ends 50, 50' of members 24, 24' are close together to allow bending of interposed segment 60 of the plate. The operating ends 62, 62' of the tools depend away from one another to allow each of the ends to be gripped without the hands being too close together. Moving ends 62, 62' inward through arcuate curves 63, 63' will transmit a bending moment to plate 77, causing interposed segment 60 to plastically buckle upward perpendicular to the plane of the plate. Forcing the tool ends outward will cause portion 60 to buckle downward. In either case, the transverse curve 79 of the plate is supported by the shaped aperture openings of the tools during the bending process.

Figure 12:
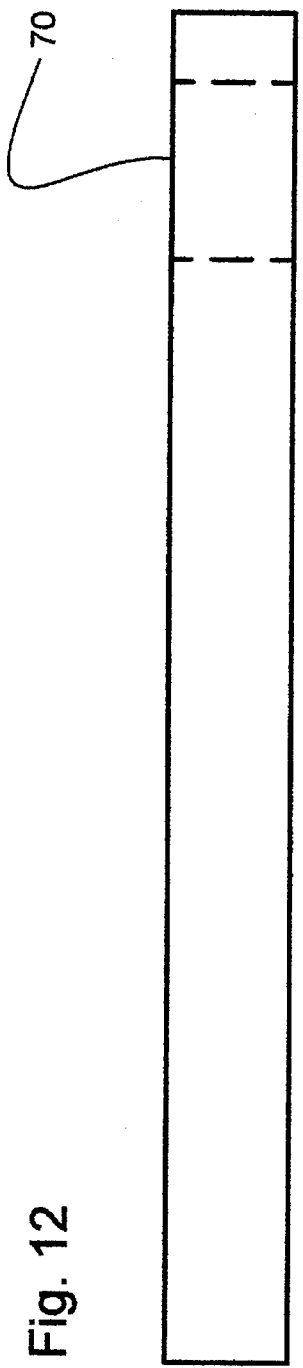
FIG. 12 is a side view of a plate bending tool in accordance with the present invention that is suitable for twisting a dynamic compression plate.
Figure 13:
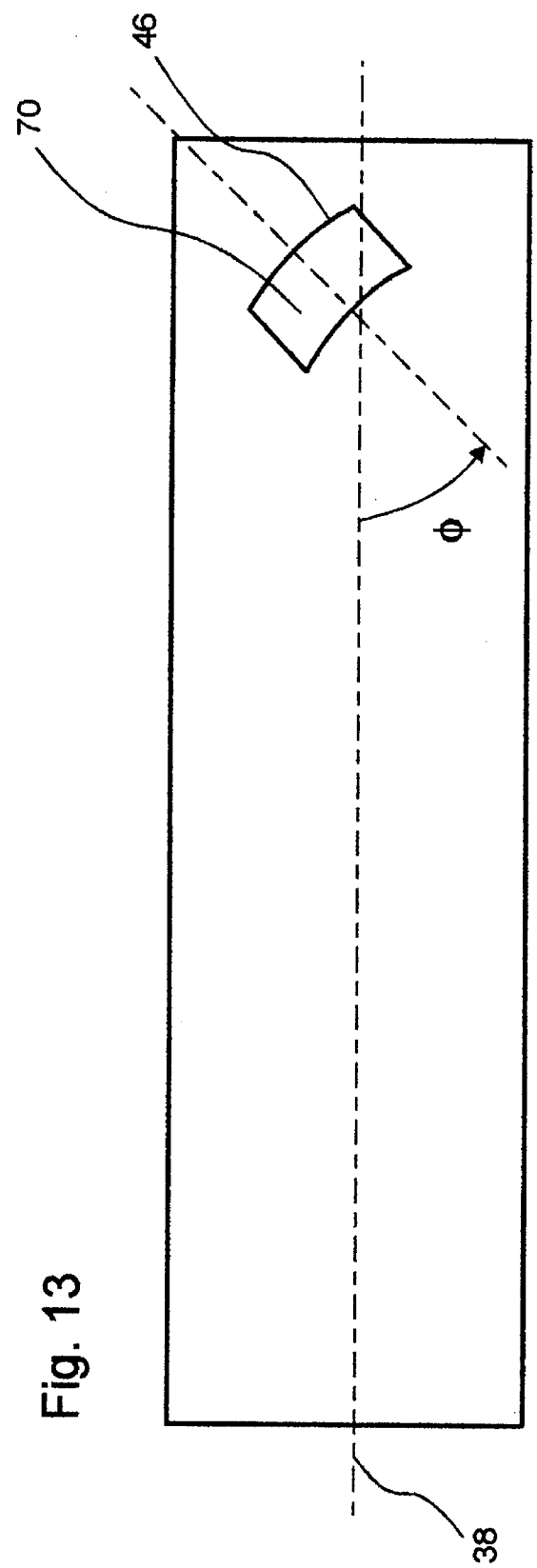
FIG. 13 is a top view of the plate bending tool of FIG. 12.

FIGS. 12 and 13 show the preferred partial embodiment of the invention for twisting compression plates around major axis A'A. Aperture 70 is oriented at a positioning angle Ø relative to a long axis of the tool and extends straight through the body of the bending tool.

Figure 14:
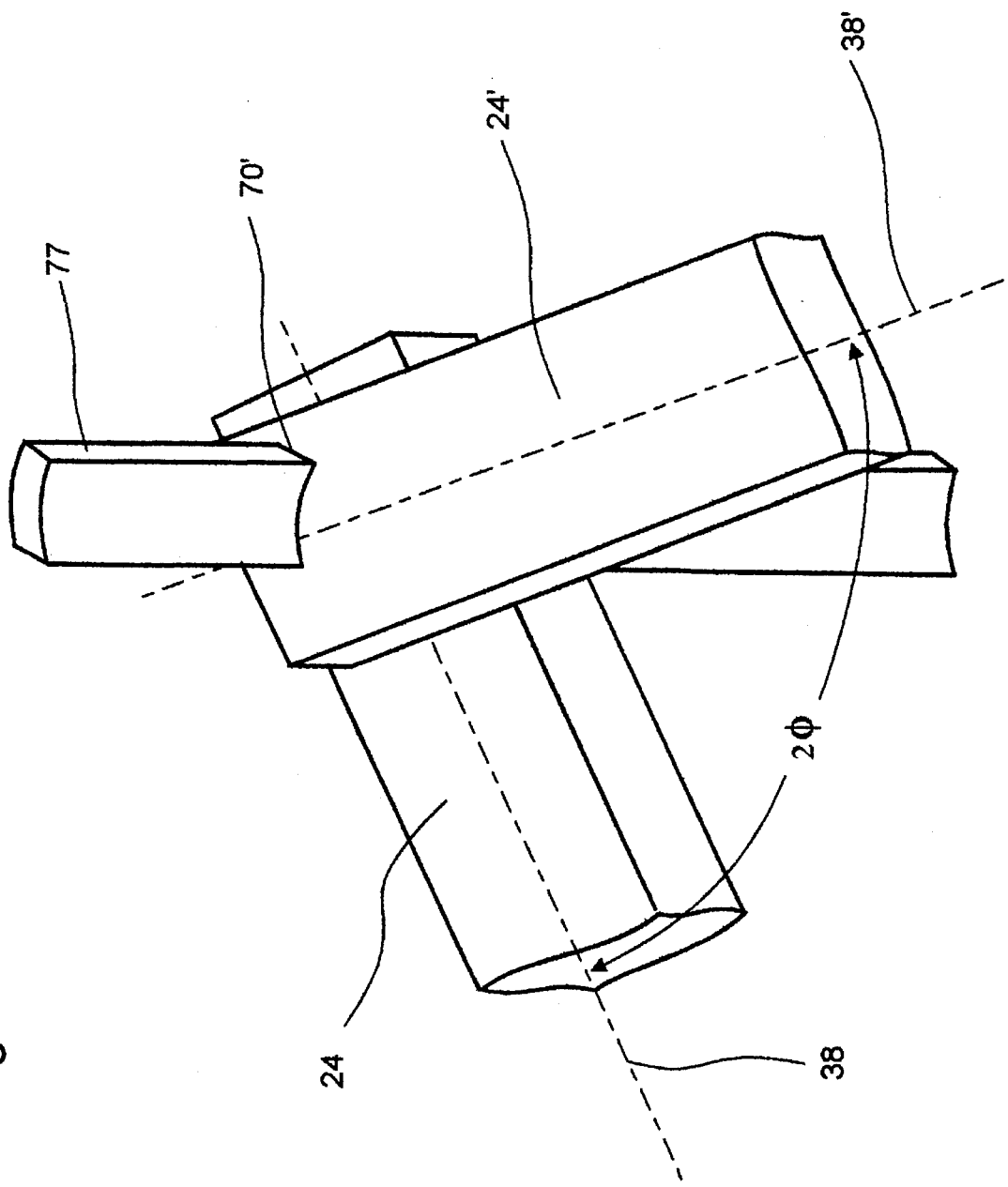
FIG. 14 is a perspective view of the working ends of two plate bending tools in accordance with the present invention positioned to twist a dynamic compression plate along its long axis.

FIG. 14 shows the bending tool of FIGS. 12 and 13 in operation. Compression plate 77 is inserted through the apertures 70, 70' of the two bending tools members 24, 24' wherein member 24' is turned over to present a complementary orientation of the second tool's aperture 70' to the first. The working ends 50, 50' (not shown) of the tools are moderately close together and the longitudinal axes 38, 38' of the two members extend away from one another at an angle equal to twice that of the aperture orientation, or 2Ø, to allow a user to grip the opposite ends with hands far enough apart for comfortable operation.

Figure 15:
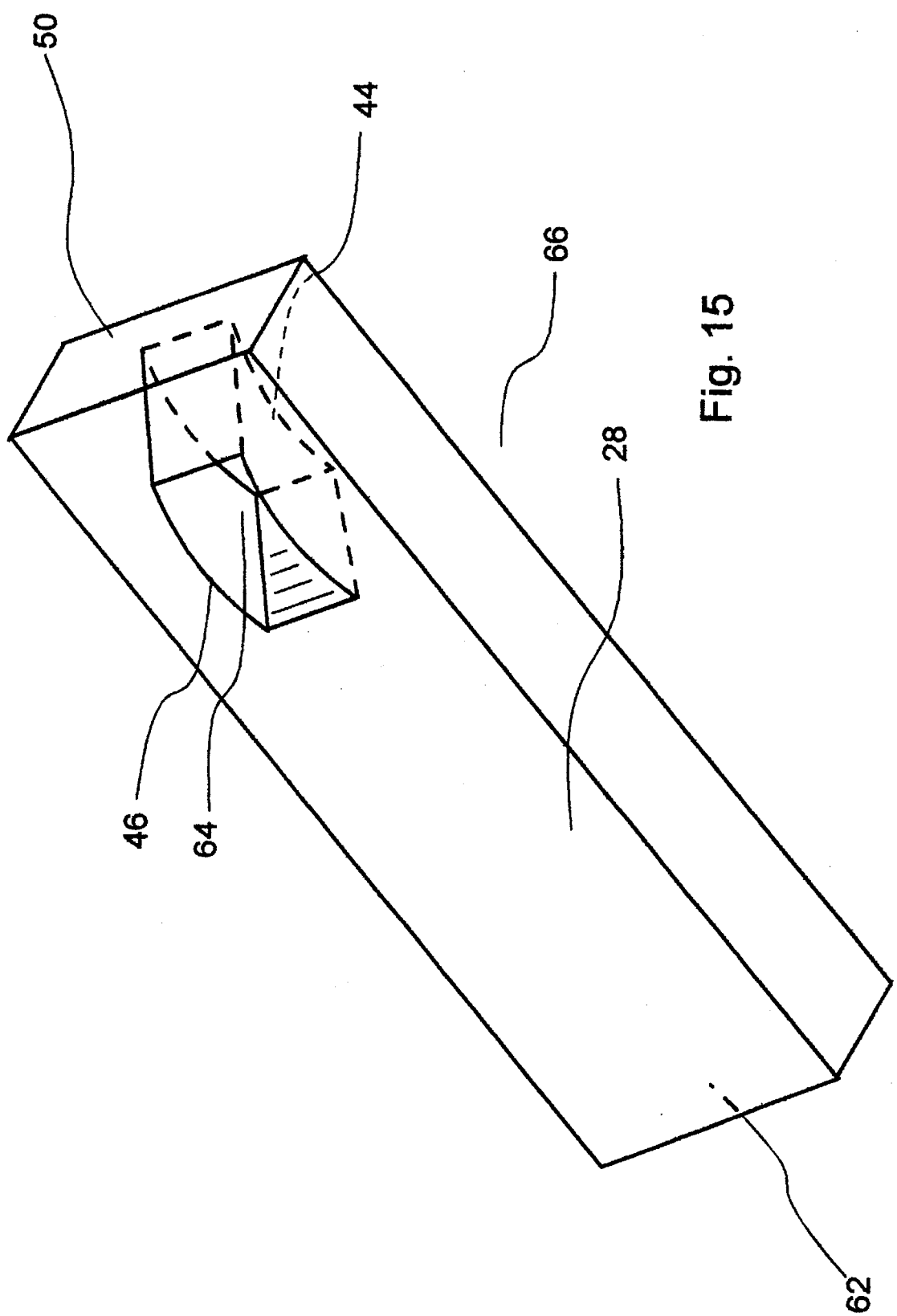
FIG. 15 is a perspective view of the working end of a plate bending tool in accordance with the present invention that is suitable for bending a dynamic compression plate in the plane of the plate.

FIG. 15 shows another preferred embodiment 66 of the invention used to bend a compression plate within the principal plane of the plate. Aperture opening 46 is oriented orthogonally on second major surface 28 so that major axis B'B of the plate is parallel to the long axis of the bending tool. The aperture 64 slopes downward between offset openings 44, 46 on tool 66 to facilitate the use of a pair of tools 66 in concert so that each working end 50 is closer together and each operating end 62 further apart.

In summary, the present invention can optimize the localization of bending forces on orthopedic bone compression plates depending upon the orientation of the aperture opening on the face of the tool and the disposition of the aperture through the tool. Specifically, the bone plate will be bent in the plane defined by the long axis of the bone plate and the long axis of the bending iron. For plate twisting, the apertures go through the bending iron approximately perpendicularly. The apertures are ideally rotated or sloped so that the long axes of the irons will intersect at a 30 to 60 angle when plates are being bent.

Each bending tool can have two or more apertures. Each aperture is generally used to perform a different function, such as bending a bone plate in its principal plane, bending a bone plate perpendicular to its principal plane, or twisting a plate along its major axis. Two bending irons are used at one time to bend or twist a plate. The working end of the tool for one partial embodiment can be the operating end of the tool for another partial embodiment.

In one preferred embodiment, each of a pair of bending irons would each fit the same bone plate size and design (see FIG. 16). The three apertures 42, 64, 70 would permit bending the plate in two planes and twisting the plate along its major axis.

FIG. 17 shows another preferred embodiment, wherein each of a pair of bending irons would have six holes. This would permit bending the three most commonly used styles and sizes of plates for broken medium sized bones perpendicular to the plane of the plate and would also permit twisting the same three plate styles. These are the two most commonly used plate contouring maneuvers.

FIG. 18 is a view of another embodiment of the invention for bending and twisting a very stout dynamic compression plate. It has been tapered to improve its strength-to-weight ratio, particularly its strength for bending a plate in the plane of the plate.

Although the present invention has been described in terms of three presently preferred embodiments, it is to be understood that such disclosure is not to be interpreted as limiting. Various alterations, modifications and combinations will no doubt become apparent to those skilled in the art after having read the above disclosure. Accordingly, it is intended that the appended claims be interpreted as covering all alterations and modifications that fall within the true spirit and scope of the invention.

I claim:

1. A tool for bending a malleable orthopedic bone plate comprising:

an elongate rigid member having a longitudinal axis, said member having first and second substantially opposed major surfaces along said longitudinal axis and first and second lateral ends, said member having a first aperture spanning front and back substantially crescent-shaped aperture openings said front and back openings having an upper curvilinear side and an opposing lower curvilinear side located on respective major surfaces adjacent the first lateral end for accepting an orthopedic bone plate having a crescent-shaped cross section, wherein the front and back crescent-shaped aperture openings are offset from one another by an oblique angle relative to a perpendicular of the longitudinal axis.

2. The tool of claim 1 wherein the oblique angle is from about 5 to 60 degrees.

3. The tool of claim 2 wherein the oblique angle is from about 10 to 45 degrees.

4. The tool of claim 3 wherein the oblique angle is from about 25 to 35 degrees.

5. A tool for bending a malleable orthopedic bone plate comprising:

an elongate rigid member having a longitudinal axis, said member having first and second substantially opposed major surfaces along said longitudinal axis and first and second lateral ends, said member having a first aperture spanning front and back substantially crescent-shaped aperture openings said front and back openings having an upper curvilinear side and an opposing lower curvilinear side located on respective major surfaces adjacent the first lateral end for accepting an orthopedic bone plate having a crescent-shaped cross section, further including an aperture axis symmetrically bisecting the front aperture opening and passing from the lower curvilinear side of the front aperture opening to the upper curvilinear side, wherein the front aperture opening is rotated so that its aperture axis is disposed at a non-zero positioning angle relative to the longitudinal axis.

6. The tool of claim 5, wherein the positioning angle is from about 5 to 40 degrees.

7. The tool of claim 5, wherein the positioning angle is 90 degrees and the front and back crescent-shaped openings are offset from one another by an oblique angle relative to a perpendicular of the longitudinal axis of the rigid member, whereby an orthopedic bone plate may be bent in the plane of the plate.

8. The tool of claim 7 wherein the oblique angle is from about 5 to 60 degrees.

9. The tool of claim 5, wherein the elongate member has a second aperture spanning second front and back crescent-shaped aperture openings located on opposing major surfaces and offset from one another by an oblique angle relative to a perpendicular of the longitudinal axis of the rigid member.

10. The tool of claim 9, wherein the elongate member has a third aperture spanning third front and back crescent-shaped openings located on opposing major surfaces, said third back opening being spatially offset from said third front opening by a second oblique angle relative to the perpendicular of the longitudinal axis of the rind member and symmetric about a third aperture axis, the third aperture axis being orthogonal to the longitudinal axis of the elongate tool member.

11. A plate bending system comprising in combination:

a first elongate bending member having a longitudinal axis, said first elongate bending member having first and second opposing major surfaces along said longitudinal axis and first and second lateral ends, said first member having a front aperture opening located on the first major surface adjacent the first lateral end, and a back aperture opening located on the second major surface having a substantially identical shape as and offset from the front opening, wherein the back and front openings are spanned by an aperture which extends through the first bending member from the front opening to the back opening at an oblique angle as measured relative to a perpendicular of the longitudinal axis of the elongate rigid member;

a second elongate bending member having a longitudinal axis, said second elongate bending member having third and fourth opposing major surfaces along said longitudinal axis and third and fourth lateral ends, said second member having a front aperture opening located on the third major surface adjacent the third lateral end, and a back aperture opening located on the fourth major surface having a substantially identical shape as and offset from the front opening, wherein the back and front openings are spanned by an aperture which extends through the second bending member from the front opening to the back opening at the oblique angle; and a malleable plate received within the aperture openings of the first and second bending members, said plate having an interposed segment adjacent and between the front aperture openings of the first and second bending members wherein said first and second bending members extend away from one another at twice the oblique angle of the aperture so that movement of the second and fourth lateral ends through an arcuate path toward each other places a bending force on the interposed segment of the malleable plate.

12. The system of claim 11 wherein the edges defined by the intersection between the first major surface and the first lateral end and the third major surface and the third lateral end are radiused to allow closer apposition of the first and second bending members.

13. The system of claim 11 wherein the front aperture openings on the first and second bending members are substantially crescent-shaped having upper and lower approximately parallel curvilinear sides connected by two side surfaces.

14. The system of claim 13 wherein the first elongate bending member further includes an aperture axis symmetrically bisecting the front aperture opening and passing from the lower curvilinear side of the front aperture opening to the upper curvilinear side, wherein the front aperture opening is rotated so that its aperture axis is disposed orthogonally to the longitudinal axis of the first member.

15. The system of claim 11 wherein the oblique angle is between approximately 5 and 60 degrees.

16. The system of claim 15 wherein the oblique angle is between approximately 10 and 45 degrees.

17. The system of claim 16 wherein the oblique angle is between approximately 25 and 35 degrees.

18. A plate bending system comprising in combination:

a first elongate bending member having first and second substantially opposed major surfaces and first and second lateral ends, said first member having a front aperture opening located on the first major surface adjacent the first lateral end, and a back aperture opening located on the second major surface wherein the back and front openings are spanned by an aperture which extends through the first bending member from the front opening to the back opening, the first member further including a longitudinal axis passing from the first to the second lateral ends of the member;

a second elongate bending member having third and fourth substantially opposed major surfaces and third and fourth lateral ends, said second member having a front aperture opening located on the third major surface adjacent the third lateral end, and a back aperture opening located on the fourth major surface wherein the back and front openings are spanned by an aperture which extends through the second bending member from the front opening to the back opening, the second member further including a longitudinal axis passing from the third to the fourth lateral ends of the member;

a malleable plate having a cross section received within the aperture openings of the first and second bending members, said plate having an interposed segment adjacent the front aperture openings of the first and second bending members wherein the front aperture openings of the first and second bending members are each rotated by a positioning angle relative to the longitudinal axis of the member such that the transverse axis of the interposed segment of the plate is disposed at the positioning angle of between 0 and 89 degrees with respect to the longitudinal axis of the first and the second elongate bending members.

19. The system of claim 18 wherein the positioning angle is approximately 0 degrees and the front and back aperture openings of at least one of the bending members are offset from one another by an oblique angle of 5 to 60 degrees as measured relative to a perpendicular of the longitudinal axis of at least one of the bending members.

20. The system of claim 18 wherein the positioning angle is between approximately 5 and 40 degrees.

21. The system of claim 18 wherein the first and second bending members are made from the same material as the plate.

22. The system of claim 18, wherein the elongate rigid member is formed of a material selected from a group consisting of stainless steel, a metal including titanium, a cobalt chromium molybdenum alloy, and a stainless steel alloy including nitrogen.

23. A method for bending orthopedic plates for accurate fitting to an irregularly shaped bone using a pair of elongate bending members, each member having substantially opposed major surfaces along a longitudinal axis spanning top and bottom lateral ends, each member further having an aperture extending through said member adjacent the top lateral end at an oblique angle as measured from a perpendicular to the longitudinal axis of the respective bending member, the method comprising:

fully enclosing within each of the apertures a first and second received segments along the length of the orthopedic plates, each received segment separated by an exposed length of the orthopedic plate, each of said segments having a first bending end adjacent the exposed length of the plate and a second bending end; and applying similarly directed force to each of the first bending ends and equal and opposite force to each of the second bending ends thereby causing the orthopedic plate along the interposed length between the two received segments to bend in a direction consistent with the force applied to the first bending ends of the received segments.

24. The method of claim 23 further including:

manually applying inwardly directed force to the bottom lateral ends of the member to buckle the exposed segment of the member perpendicular to a principal plane of the plate.

25. The method of claim 23 wherein the transverse axis of the first and second received segments of the orthopedic plates is disposed at a predetermined angle relative to the longitudinal axis of respective major surfaces, thereby allowing the orthopedic plates to be bent in the plane of the plate.

26. The method of claim 23 wherein one aperture of the pair of elongate members has at least one curvilinear edge.

* * * * *